United States Patent [19]
Correas

[11] Patent Number: 6,112,120
[45] Date of Patent: Aug. 29, 2000

[54] APPARATUS FOR CONNECTING A PROBE CONNECTOR AND AN ACTIVE IMPLANTABLE MEDICAL DEVICE

[75] Inventor: Philippe Correas, Montmorency, France

[73] Assignee: ELA Medical S.A., Montrouge, France

[21] Appl. No.: 09/109,325

[22] Filed: Jul. 2, 1998

[30] Foreign Application Priority Data

Jul. 3, 1997 [FR] France .................................. 97-08429

[51] Int. Cl.⁷ .................................................. A61N 1/375
[52] U.S. Cl. ............................................. 607/37; 439/909
[58] Field of Search .................................. 607/37, 2, 36, 607/115, 116, 119, 122; 439/909, 374, 816, 820, 824, 826, 460

[56] References Cited

U.S. PATENT DOCUMENTS 4,712,557 12/1987 Harris .
4,860,750 8/1989 Frey et al. .

FOREIGN PATENT DOCUMENTS 3712633 10/1987 Germany .......................... H01R 4/50

WO 91/04069 4/1991 WIPO ............................. A61N 1/00

*Primary Examiner*—Kennedy J. Schaetzle
*Attorney, Agent, or Firm*—Orrick, Herrington & Sutcliffe LLP

[57] ABSTRACT

Apparatus for mechanically immobilizing a probe connector in a generator connector of an active implantable medical device, especially for a cardiac pacemaker, defibrillator and/or cardiovertor. The active implantable medical device comprises a generator connector (10) with an axial female cavity (26) receiving a probe connector (24), at least one connection output (12, 14) and apparatus for the mechanical immobilisation the probe connector in the cavity. The connection output exerts a radial support pressure of the output conducting element (16, 18) against a corresponding conducting element (20, 22) of the probe connector to achieve an adequate electrical connection. Separate from the electrical contacts at the connection outputs, and at the outlet of the cavity, a locking wedge (38) is inserted and held in place between an external surface (46) of the probe and an internal surface (48) of the cavity to achieve a mechanical immobilization of the probe in the generator connector.

19 Claims, 1 Drawing Sheet

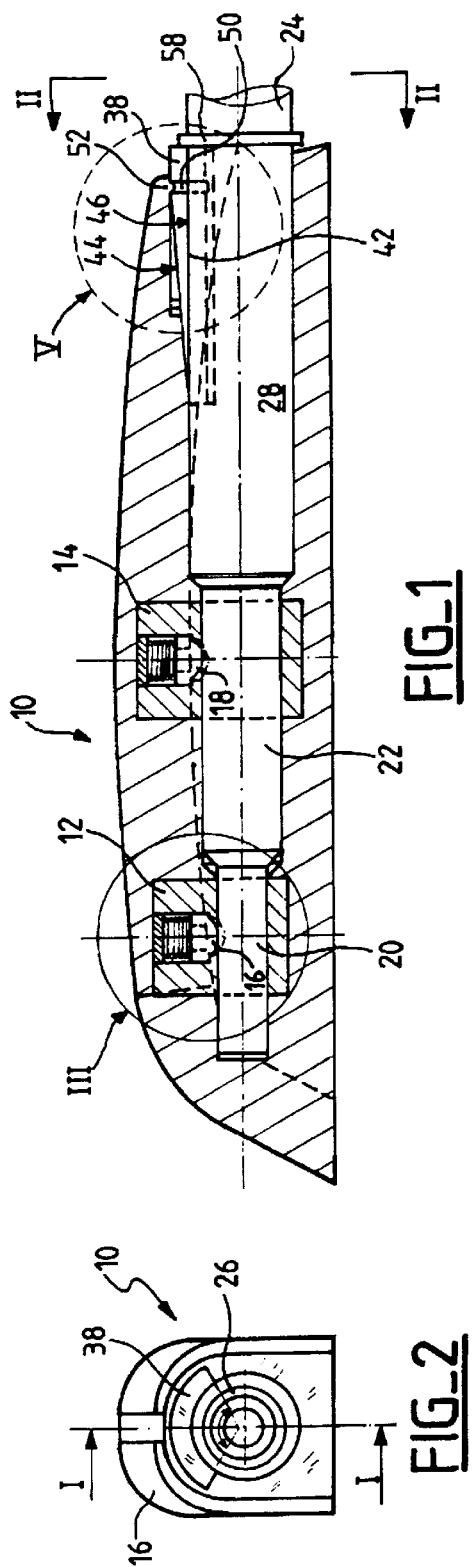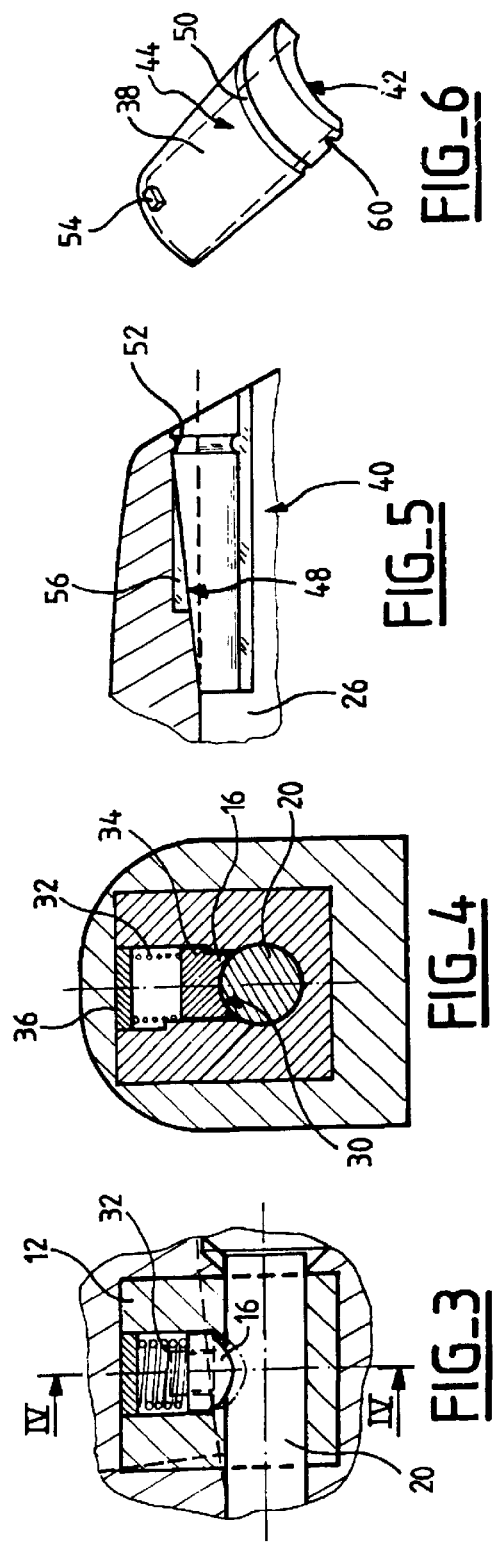

APPARATUS FOR CONNECTING A PROBE CONNECTOR AND AN ACTIVE IMPLANTABLE MEDICAL DEVICE

FIELD OF THE INVENTION

The present invention concerns active implantable medical devices. Although it will be mainly described in the case of a cardiac pacemaker, as an example of an embodiment of the invention, the invention also is applicable in a far more general manner to a great variety of "active implantable medical devices," as such devices are defined by the Jun. 20, 1990 Directive 90/385/CEE of the European Community Council, which definition includes, in addition to cardiac pacemakers, defibrillators and/or cardiovertors, neurological devices, infusion pumps of medical substances, cochlear implants, implanted biological sensors (collectors), etc.

BACKGROUND OF THE INVENTION

These active implantable medical devices comprise a case generally designated as a "generator" or "pulse generator" connected electrically and mechanically to a probe (also called a lead or electrode, depending on its functionality), which connection is made by the surgeon at the time of implantation.

To this end, one can refer to the European and French standard NF EN 50077 entitled "Connector with low profile for implantable cardiac pacemakers," which defines a normalised connection system called "IS-1" for the interchangability of probes and pulse generators produced by different manufacturers. However, as noted, the invention is not limited to the particular case of connection systems according to this standard, nor is it limited to connection systems for cardiac pacemakers.

Up until now, the connection between the connector of the probe and the connector of the generator was realised by one or more screws, manipulated by the surgeon by means of an ad-hoc tool (a screwdriver supplied with a torque limitation) at implantation. This connection by screws presents, however, several disadvantages. In the first place, besides requiring a specific tool for its use (which must be supplied), this technique imposes the presence of tight seals which allow for the passage of this tool (to avoid that, after implantation, the connection output does not come in contact with organic fluids). This requirement of tightness at the location where the tool penetrates the seal to turn the screw implies an additional cost and an increase of the size of the generator at the location of the connector.

In addition, this connection system is not free from the forgetfulness of the surgeon in tightening the screw, an insufficient tightening of the screw, or an over-tightening of the screw and damaging the device (e.g., stripping the threads).

OBJECTS AND SUMMARY OF THE INVENTION

It is, therefore, an object of the present invention to overcome the inconvenience of the known connection system and to propose a connection system that insures the mechanical and electrical connection of the probe to the generator and avoids the use of tightening screws.

As one will see, the mechanism of the present invention allows, nevertheless, to insure an excellent mechanical immobilisation of the probe on the generator, by avoiding therefore all risk of an inopportune disconnection. In addition, the invention remains perfectly compatible with, notably, the dimensional mechanical standard IS-1, in that it allows accepting without modification all actual and future probes meeting the existing standard.

To this end, the active implantable medical device of the present invention, which comprises a generator connector comprising an axial female cavity receiving a probe connector, at least one electrical connection output, and a means of mechanical immobilisation of the probe connector in the cavity, the generator electrical connection output comprising means to exert a radial support pressure on an electrical conducting element of the generator connection output against an electrical conducting element of the probe connector, characterised in that means of immobilisation are distinct from the electrical connection outputs and comprise, at the outlet of the cavity, a locking wedge able to be inserted and held in place by a force fit between an external surface of the probe and an internal surface of the cavity.

Preferably, the locking wedge presents, in longitudinal section, a cuneiform profile on the internal surface of the cavity which has a groove, preferably conical, whose surface forms a slope similar to the cuneiform profile of the locking wedge.

In one preferred embodiment, the locking wedge comprises a cylindrical surface able to come in contact with the external surface of the probe, and a conical surface able to come in contact with the internal surface of the cavity.

Preferably, in a radial plane, the wedge spreads circumferentially over an angular sector of an aperture comprised between 90° and 120°.

It also is foreseen to have a means of interlocking the wedge in the cavity in the operating position. Preferably, the interlocking means is a groove formed in the wedge which co-operates and interlocks with a protruding relief formed in the cavity, such that the groove and relief spread over a portion of the circumference in the radial plane. Alternatively, the groove could be in the cavity and the relief on the wedge, and other complementary interlocking structures could be used.

It also is foreseen to have in addition a retention means to keep the locking wedge in place in the cavity in the absence of a probe. Preferably, the retention means comprises a spur positioned in a proximal position to act as a stop, co-operating with a relief of the cavity in the distal position.

Further, the generator output connection means operates to exert a radial support pressure, and preferably includes a means of elastically urging the conducting element of the output against the conducting element of the connector. The elastic urging means is preferably a spring.

In a preferred embodiment, the probe also comprises a shoulder to engage axially the locking wedge in the sense of force-fitting the wedge during the insertion of the probe in the cavity.

BRIEF DESCRIPTION OF THE DRAWINGS

Others characteristic features and advantages of the present invention will appear to a person of ordinary skill in the art in view of the following detailed description of a preferred embodiment of the present invention, in which like reference characters refer to like parts, and in which:

FIG. 1 is a longitudinal cross sectional view, taken along line I—I of FIG. 2, of a connection system according to the present invention, with a probe connector inserted in a generator connector;

FIG. 2 is a rear view, taken along lines II—II of FIG. 1;

FIG. 3 is an enlarged view of the detail of area III of FIG. 1, showing one of the outputs;

FIG. 4 is a cross sectional view taken along line IV—IV of FIG. 3;

FIG. 5 is an enlarged view of the detail of area V of FIG. 1, showing the form of the cavity of the generator connector at this position; and FIG. 6 is an enlarged perspective view of the locking wedge of the probe in the generator cavity.

DETAILED DESCRIPTION OF THE DRAWINGS

On the figures, the reference 10 designates in a general manner the upper part of the pulse generator of a cardiac pacemaker, in this example a generator adapted to receive a bipolar endocardial probe, having two connection outputs 12, 14 embedded in an isolating body, for example, an epoxy resin. The connection outputs 12, 14 include element drivers 16, 18 coming in support against respective coaxial conducting surfaces 20, 22, axially offset, of the probe 24 in a manner that is well known and conventional in the case of bipolar probes, especially probes that conform to the aforementioned dimensional mechanical standard IS-1.

Apart from the surface regions 20, 22 which are destined to establish the electrical connection, the probe 24 presents an external surface in the form of a cylindrical body 28, made of a material or having a sheath material that is slightly deformable (typically a silicone polymer), that comes to lodge in a cavity 26 (see FIGS. 2 and 5, which are views without the probe). This cavity 26 can be in particular compliance with the prescriptions of the aforementioned standard IS-1.

FIGS. 3 and 4 illustrate in more detail the two probe connection contacts 12 and 14, which in this embodiment are structurally identical and thus only one is discussed.

In the traditional connector of the prior art, the connection outputs insure both the electrical connection and the mechanical connection between the probe and generator connector by a system of screws. In contrast, in the present invention, the generator connector outputs are different in that they only function to insure the electrical connection between generator output contact elements 16, 18 and the probe connection contacts 20, 22. The contact element 16 of the generator output 12 (and similarly for the contact element 18 of the other generator output 14) includes a concave support surface 30 having a cylindrical form, which is complementary to the convex cylindrical form of the surface 20 in a manner to engage therewith in close fitting contact and support. The contact element 16 is extended radially by an elastic element, such as a spring 32, in a manner to obtain a sufficient force of support such that the contact resistance (i.e., impedance) between the element 16 and the conducting surface 20 be as low as possible. In order that the concave surface 30 is presented in the proper direction, as compared to the extremity of the probe, it is foreseen to include a guide, such as a groove 34, to prevent element 16 from turning in its cavity. The assembly is, for example, set in element 36 in a manner to form a monobloc contact output, without especially the passage seals that were necessary with the connector outputs of the prior art. The assembly according to the invention is therefore perfectly tight, and the electrical elements are isolated without risk of contact with corporal (body) fluids.

To insure the mechanical maintenance of the extremity of probe 24 in the generator connector, it is foreseen, according to the invention to employ, a locking wedge 38 (represented in an isolated manner in FIG. 6) which is inserted between the probe and generator connector cavity. Wedge 38 is formed of a rigid material, such as a resin epoxy, with the result that it is forcibly inserted between the body of the generator connector (also a rigid material such as a resin epoxy) and the exterior surface (sheath) 28 of the probe 24 (a material that is deformable, such as a silicone resin). The wedge 38 thus maintains a mechanical connection between these two elements due to the fact of the elasticity of the exterior surface part of the probe being slightly deformed by the wedge 38 near the distal outlet of the generator cavity 26.

Further, the wedge 38 has a longitudinal axis and, in its longitudinal section cuneiform shape, e.g., a form that is bevelled, corresponding to a hollow or groove 40 (FIG. 5) longitudinally formed in the interior surface of cavity 26. More precisely, the wedge 38 presents, inwardly, a cylindrical surface 42 having a similar radius as the external cylindrical surface 46 of the probe body 28 in a manner to conform therewith, and a tronconic (truncated conical section) external surface 44 corresponding to an inward surface that is equally tronconic and similarly angled at the apex 48 of the groove 40 (FIG. 5).

In a radial plane, as illustrated in FIG. 2, the wedge 38 spreads circumferentially over an angular sector of angle a, typically selected from between 90° and 120°. This characteristic is not, however, restrictive and the wedge 38 can, for example, spread over a greater angular section, or even over almost all of the circumference, in this latter case forming a split conical ring.

Advantageously, it is foreseen to interlock the wedge in the inserted position, for example, using some interlock means of interlocking. One such interlock means may be in the form of a circumferential groove 50 (FIGS. 1 and 6) co-operating with a corresponding circumferential relief (protrusion) 52 (FIGS. 1 and 5) of the cavity 40.

Furthermore, to maintain the wedge 38 in position in the groove 40 in the absence of a probe in the cavity 26, it is foreseen to include a retention means, for example, a structure in the form of a spur (or boss) 54 susceptible to come to rest against a corresponding relief 52 when the wedge is in its extreme output position at the groove 40. Of course, it also is foreseen to have a longitudinal slot 56 (FIG. 5) positioned in the groove 40 to avoid the spur 54 from preventing a good conical surface contact between surfaces 44 and 48 when the wedge 38 is fully inserted, in the proximal direction, in the groove 40.

One will understand that, after the insertion of the probe at the bottom of the cavity 26, it suffices to push in a proximal direction the wedge 38 in the groove 40 until it is immobilised and interlocked. This wedge 38 is going to deform slightly the exterior surface of the probe connector, due to the fact of the elastic character of the material of the sheath, to put it in place in the groove. The wedge 38 can be placed or loaded in the groove by the physician-therapist at the moment of the setting of the connector.

One also can anticipate on the probe conductor a shoulder 58, placed at a distance such that the insertion of the probe in the groove 40 comes at the same time as pushing the wedge, thus realising simultaneously the placement in electrical contact and in mechanical connection of the probe connector on the generator connector.

To permit disconnection of the probe from the generator, one can anticipate a detent 60 (FIG. 6) allowing an appropriate tool to be used to engage the wedge 38, for example, to grasp the wedge and extract it or to exert a sufficient pressure to flex wedge 38 to release the groove from the relief 52, and thus unlock any interlocking system.

One skilled in the art will appreciate that the present invention can be practised by other than the described embodiments, which are presented for purposes of illustration and not of limitation.

I claim:

1. An active implantable medical device, comprising a generator connector including an axial female cavity having an internal surface to receive an external surface of a probe connector and an outlet, at least one connection output in said cavity, and means for mechanically immobilizing the probe connector in the cavity, the at least one connection output comprising an electrical conducting element and means for exerting a radial support pressure on said electrical conducting element and against a conducting element of the external surface of the probe connector, wherein the immobilizing means is distinct from the at least one connection output and further comprises a locking wedge to be forcibly inserted between the probe external surface and the cavity internal surface at an outlet of the cavity, said wedge having a longitudinal axis and a cuneiform profile in section along said axis.

2. The device of claim 1, wherein the cavity internal surface comprises a groove having a surface which forms a slope corresponding to the cuneiform profile of the locking wedge to receive therein the locking wedge.

3. The device of claim 1, wherein the locking wedge comprises a cylindrical surface configured to contact the probe external surface and a conical surface configured to contact with the cavity internal surface.

4. The device of claim 1, in which, in a radial plane, the wedge spreads circumferentially over an angular sector of an angle selected from between 90° and 120°.

5. The device of claim 1, further comprising means for interlocking the wedge in an operating position in the cavity.

6. The device of claim 5, wherein the interlocking means comprises a groove and a complementary relief, wherein one of the groove and the relief is formed in the wedge and the other of the groove and the relief is formed in the cavity, and wherein the groove and relief extend a portion around a circumference in a radial plane and cooperate to interlock the wedge and the cavity.

7. The device of claim 1, further comprising means for retention of the locking wedge in the cavity in the absence of a probe.

8. The device of claim 7, wherein the retention means comprises a spur in a proximal position on the wedge, co-operating with a relief of the cavity in a distal position distal relative to said proximal position.

9. The device of claim 1, wherein the at least one connection output further comprises means for elastically urging the at least one connection conducting element against the probe connector conducting element.

10. The device of claim 1, wherein the probe further comprises a shoulder to retain axially the locking wedge during the forced insertion of the probe in the cavity.

11. Apparatus for connecting a probe to an active implantable medical device, comprising:

a generator connector including an axial female cavity having an internal surface and an outlet to receive an external surface of a probe connector and at least one connection output, the connection output comprising a radial support pressure element coupled to a conducting element to urge said conducting element against a conducting element on the external surface of the probe connector in electrical contact therewith; and a locking wedge insertable between the probe external surface and the cavity internal surface at the outlet of the cavity, said wedge having a longitudinal axis and a cuneiform profile in section along said axis.

12. The apparatus of claim 11, in which the internal surface of the cavity comprises a groove having a surface which forms a slope of the cuneiform profile of the locking wedge.

13. The apparatus of claim 11, further comprising a groove and a complementary relief, wherein one of the groove and the relief is formed in the wedge and the other of the groove and the relief is formed in the cavity and the groove and the relief extend a fraction around the circumference in a radial plane and cooperate to interlock the wedge and the cavity.

14. The apparatus of claim 11, further comprising a spur in a proximal position on said wedge, co-operating with a relief in a distal position of the cavity.

15. The apparatus of claim 11, wherein the connection output further comprises an elastic element to produce the radial support pressure on the conducting element.

16. The apparatus of claim 11, wherein the probe further comprises a shoulder to retain axially the locking wedge during a forced insertion of the probe in the cavity.

17. The apparatus of claim 11, wherein the locking wedge further comprises a cylindrical surface configured to contact the probe external surface and a conical surface configured to contact with the cavity internal surface.

18. The apparatus of claim 17 in which the internal surface of the cavity comprises a conical groove having a surface which corresponds to the profile of the locking wedge.

19. The apparatus of claim 11, in which, in a radial plane, the locking wedge spreads along a circumference over an angular sector of an angle selected from between 90° and 120°.

* * * * *

UNITED STATES PATENT AND TRADEMARK OFFICE
CERTIFICATE OF CORRECTION

PATENT NO. : 6,112,120
DATED : August 29, 2000
INVENTOR(S) : Philippe Correas

It is certified that error appears in the above-identified patent and that said Letters Patent is hereby corrected as shown below:

Title page, Item [54] and Column 1, line 1,
Title, after "APPARATUS" insert -- WITH LOCKING WEDGE --

Title page,
Item [57], ABSTRACT,
Lines 7-8, after "mechanical" delete "immobolisation" and insert
-- immobilization of --;

Column 1,
Line 29-30, before "connection" delete "normalised" and insert -- normalized -- and after "for the" delete "interchangability" and insert -- interchangeability --
Line 35, before "by one" delete "realised" and insert -- realized --
Lines 64-65, after "mechanical" delete "immobilisation" and insert -- immobilization --

Column 2,
Line 8, after "mechanical" delete "immobilization" and insert -- immobilization --.
Line 13, after "connector" delete "characterised" and insert -- characterized --; and after "means of" delete "immobilisation" and insert -- immobilization--
Lines 32-33, after "wedge which" delete "co-operates" and insert -- cooperates --
Lines 43-44, after "stop" delete "co-operating" and insert -- cooperating --
Lines 56, before "characteristic" delete "Others" and insert -- Other --

Column 3,
Line 1, after "cross" insert -- - --;
Lines 46, after "close" insert -- - --;
Line 64, after "invention" insert -- , --; and after "employ" delete ","

Column 4,
Lines 30-31, after "6)" delete "co-operating" and insert -- cooperating --
Lines 47-48, after "it is" delete "immobolised" and insert -- immobilized --
Lines 57, after "thus" delete "realising" and insert -- realizing --
Line 67, after "can be" delete "practised" and insert -- practiced --

UNITED STATES PATENT AND TRADEMARK OFFICE
CERTIFICATE OF CORRECTION

PATENT NO.   : 6,112,120
DATED        : August 29, 2000
INVENTOR(S)  : Philippe Correas It is certified that error appears in the above-identified patent and that said Letters Patent is hereby corrected as shown below:

Column 5,
Lines 45-46, before "with a" delete "co-operating" and insert -- cooperating --; and after "distal position" insert -- , --

Column 6,
Line 29, after "wedge" delete "co-operating" and insert -- cooperating --

Signed and Sealed this

Nineteenth Day of October, 2004

JON W. DUDAS
*Director of the United States Patent and Trademark Office*